United States Patent
Hirayama et al.

(10) Patent No.: US 6,791,335 B2
(45) Date of Patent: Sep. 14, 2004

(54) SAMPLE ASSEMBLY FOR THERMOELECTRIC ANALYZER

(75) Inventors: Taisei Hirayama, Akishima (JP); Masanobu Inami, Fussa (JP); Shuichi Matsuo, Oume (JP); Koichiro Ito, Osaka (JP); Ryo Hattori, Tokyo (JP); Yoshitugu Yamamoto, Tokyo (JP); Yoshihiro Notani, Tokyo (JP); Shinichi Miyakuni, Tokyo (JP)

(73) Assignees: Rigaku Corporation, Tokyo (JP); Mitsubishi Denki Kabushiki Kaisha, Tokyo (JP)

( * ) Notice: Subject to any disclaimer, the term of this patent is extended or adjusted under 35 U.S.C. 154(b) by 34 days.

(21) Appl. No.: 09/941,879

(22) Filed: Aug. 29, 2001

(65) Prior Publication Data

US 2002/0024349 A1 Feb. 28, 2002

(30) Foreign Application Priority Data

Aug. 29, 2000 (JP) ........................................ 2000-259868

(51) Int. Cl.$^7$ ............................................... G01N 25/00
(52) U.S. Cl. ........................... 324/451; 324/755; 374/45
(58) Field of Search ............................... 324/451, 158.1, 324/106, 755, 757, 765–766; 374/45, 20; 438/14–18, 106, 118, 119

(56) References Cited

U.S. PATENT DOCUMENTS

| | | | | |
|---|---|---|---|---|
| 4,320,344 A | * | 3/1982 | Nicholas | 324/451 |
| 4,542,345 A | * | 9/1985 | Tomasulo | 324/451 |
| 4,920,319 A | * | 4/1990 | Viertl | 324/451 |
| 5,126,813 A | * | 6/1992 | Takahashi et al. | 257/417 |
| 5,441,343 A | * | 8/1995 | Pylkki et al. | 374/137 |
| 6,251,696 B1 | * | 6/2001 | Ikeya et al. | 438/17 |
| 6,570,390 B2 | * | 5/2003 | Hirayama et al. | 324/501 |

OTHER PUBLICATIONS

Tomozane, Mamoru et al, "Analysis of Thermally Stimulated Current Spectroscopy in Semiinsulation GaAs. I. Initialization", Japanese Journal of Applied Physics, Feb. 1988, pp. 260–268, 27 (2), Japan.

Reber, Jr., Richard et al., "Thermally stimulated current measurements of $SiO_2$ defect density and energy in irradiated metal–oxide–semiconductor capacitors", Rev. Sci. Instrum., Dec., 1992, pp. 5714–5725, 63 (12), USA.

* cited by examiner

Primary Examiner—Evan Pert
Assistant Examiner—Paresh Patel
(74) Attorney, Agent, or Firm—Frishauf, Holtz, Goodman & Chick, P.C.

(57) ABSTRACT

In a sample assembly for a thermoelectric analyzer, typically TSC (Thermally Stimulated Current) analyzer, a sample is fixed to an electrically-insulating substrate via an adhesive layer. The material of the adhesive layer is indium or gold-tin alloy. The substrate has a pair of junction electrode layers formed thereon and a pair of electrode layers formed on the same plane of the sample. One of the electrode layers is connected with one of the junction electrode layers by electrically-conductive wire, while the other of the electrode layers is connected with the other of the junction electrode layers by another electrically-conductive wire. The substrate is made of preferably made of a highly electrically-insulating and highly thermally-conductive material which may be, for example, aluminum nitride (AlN), boron nitride (BN), beryllium oxide (BeO) or aluminum oxide ($Al_2O_3$). The sample may preferably be a compound semiconductor such as GaAs.

13 Claims, 5 Drawing Sheets

SAMPLE ASSEMBLY FOR THERMOELECTRIC ANALYZER

BACKGROUND OF THE INVENTION

This invention relates to a sample assembly for a thermoelectric analyzer which can measure an electric property of a sample as the sample temperature varies. Means for measuring an electric property of a sample during sample temperature variation includes typically a TSC (Thermally Stimulated Current) method and other measurement means such as DEA (Dielectric Analysis: thermal relaxation measurement), DLTS (Deep Level Transient Spectroscopy), ICTS (Isothermal Capacitance Transient Spectroscopy), TSIC (Thermally Stimulated Ionic Current), IV (Current-Voltage characteristic) and CV (Capacitance-Voltage characteristic). This invention relates to a sample assembly for a thermoelectric analyzer which can perform any one of these measurement methods.

The TSC method is one of the traditional methods known in the field of thermal analysis and can measure a current occurring in the sample as the sample temperature varies, the result of measurement being analyzed in various ways. It is known that the crystal defect in a sample can be analyzed using the TSC method. For example, in Japanese Journal of Applied Physics, Vol. 27, No. 2, 1988, pp.260–268 (referred to hereinafter as the first publication), a semi-insulating GaAs (gallium arsenite) sample was so analyzed that a TSC spectrum was measured in a low temperature range from the liquid helium temperature to the room temperature to analyze the deep level traps. Further, in Rev. Sci. Instrum., Vol. 63, No. 12, 1992, p.5714–5725 (referred to hereinafter as the second publication), a $SiO_2$ (silicon dioxide) layer of a MOS capacitor was so analyzed that a TSC spectrum was measured in a temperature range from the room temperature to 300° C. to analyze the density of positive holes or electrons.

In these publications, there was the following disclosure regarding a sample assembly. In the first publication, the GaAs sample has the top surface which has a central region covered with a semitransparent aluminum electrode (which becomes one of the electrodes). The top surface of the sample has also a periphery on which a guard ring is formed. On the other hand, the sample has the back surface which is covered with a thick aluminum film (which becomes the other of the electrodes). It is noted that, in the figure of the first publication, although the sample is mounted on a support which can be heated, it is not clear in what manner the sample has been mounted on the support.

In the second publication, a sample is mounted on an insulating substrate. The substrate has both ends to which stainless steel pins are fixed along with aluminum washers. An aluminum wire is connected between the washer at one end of the substrate and the back electrode of the sample ($SiO_2$ capacitor). The sample, having the back side to which the wire has been connected, is fixed at its back electrode to the center of the substrate by silver past including epoxy resin. Besides, the sample has, on its top surface, a gate which is connected with the other washer at the other end of the substrate via another aluminum wire.

As to the sample assembly disclosed in the first publication, there is no disclosure regarding a specific manner for fixing the sample to the substrate, therefore, its bonding quality can not be judged. As to the sample assembly disclosed in the second publication, the silver paste is used for bonding the sample to the substrate, raising a problem of poor temperature uniformity in the sample.

Further, since the aluminum washers and aluminum wires are used and the electric circuit, from the sample to the stainless steel pins at the both ends of the substrate, is not mirror-symmetrical, a contact-electromotive force may become large and a thermoelectromotive force may occur during the temperature increase or decrease, resulting in measurement noise.

SUMMARY OF THE INVENTION

It is an object of the invention to provide a sample assembly, for a thermoelectric analyzer, having good temperature uniformity and generating a small contact-electromotive force and a small thermoelectromotive force.

A sample assembly for a thermoelectric analyzer according to the invention includes an electrically-insulating substrate to which a sample is fixed via an adhesive layer. The material of the adhesive layer is indium or gold-tin alloy. The substrate has a pair of junction electrode layers formed thereon. The sample has a pair of electrode layers formed on the same plane of the sample. One of the electrode layers is connected with one of the junction electrode layers by an electrically-conductive wire, while the other of the electrode layers is connected with the other of the junction electrode layers by another electrically-conductive wire.

The indium used for the adhesive layer has high thermal conductivity, resulting in good heat conduction between the sample and the substrate and therefore good temperature uniformity in the sample. Besides, the indium is soft metal, so that it solves the below-described problem. Under the condition of wide-range temperature variation (for example, between the liquid nitrogen temperature and the room temperature), a thermal stress may occur between the sample and the substrate because of different rates of thermal expansion. The indium can absorb the thermal stress so that internal strain hardly occurs in the sample. The indium may be replaced by gold-tin alloy, for example, 88% Au-12% Sn, which also has good thermal conductivity.

The substrate is made of preferably a highly electrically-insulating and highly thermally-conductive material which may be aluminum nitride (AlN), boron nitride (BN), beryllium oxide (BeO) or aluminum oxide ($Al_2O_3$).

The sample assembly is adapted to be supported by two support rods. Gold washers are preferably inserted between the support rods and the junction electrode layers, decreasing the influence, on the substrate, of the thermal displacement of the support rods.

Each of the electrode layers on the sample and the junction electrode layers on the substrate may be made of a multilayer including the top layer which is preferably a gold layer. In that case, gold wires are bonded to the gold layers. The bonding between two gold parts decreases a contact-electromotive force and a thermoelectromotive force which may occur between the wires and the electrode layers and between the wires and the junction electrode layers. Furthermore, the pair of electrode layers on the sample and the pair of junction electrode layers on the substrate may be arranged mirror-symmetrical with respect to the center of the sample, so that the contact-electromotive force and the thermoelectromotive force mentioned above can be cancelled even when such forces occur.

The sample assembly may be applied to typically a TSC (Thermally Stimulated Current) analyzer or any other thermoelectric analyzer which can perform thermoelectric analysis such as DEA (Dielectric Analysis: thermal relaxation measurement), DLTS (Deep Level Transient Spectroscopy), ICTS (Isothermal Capacitance Transient Spectroscopy) TSIC (Thermally Stimulated Ionic Current), IV (Current-Voltage characteristic) or CV (Capacitance-Voltage characteristic). The sample may be preferably compound semiconductor such as GaAs.

The sample assembly for a thermoelectric analyzer according to the invention has the following advantages. The adhesive layer made of indium or gold-tin alloy is used to bond the sample with the substrate, resulting in good temperature uniformity in the sample. The gold washers are inserted between the support rods and the junction electrode layers on the substrate, decreasing the influence of the thermal displacement of the support rods. Each of the electrode layers on the sample and the junction electrode layers on the substrate includes the top layer which is a gold layer and the gold wires are bonded to the gold layers, resulting in a small contact-electromotive force and a small thermoelectromotive force. The pair of the electrode layers on the sample and the pair of the junction electrode layers on the substrate are arranged mirror-symmetrical, so that the contact-electromotive force and the thermoelectromotive force mentioned above can be cancelled even when such forces occur.

DETAILED DESCRIPTION OF THE PREFERRED EMBODIMENTS

Figure 1:
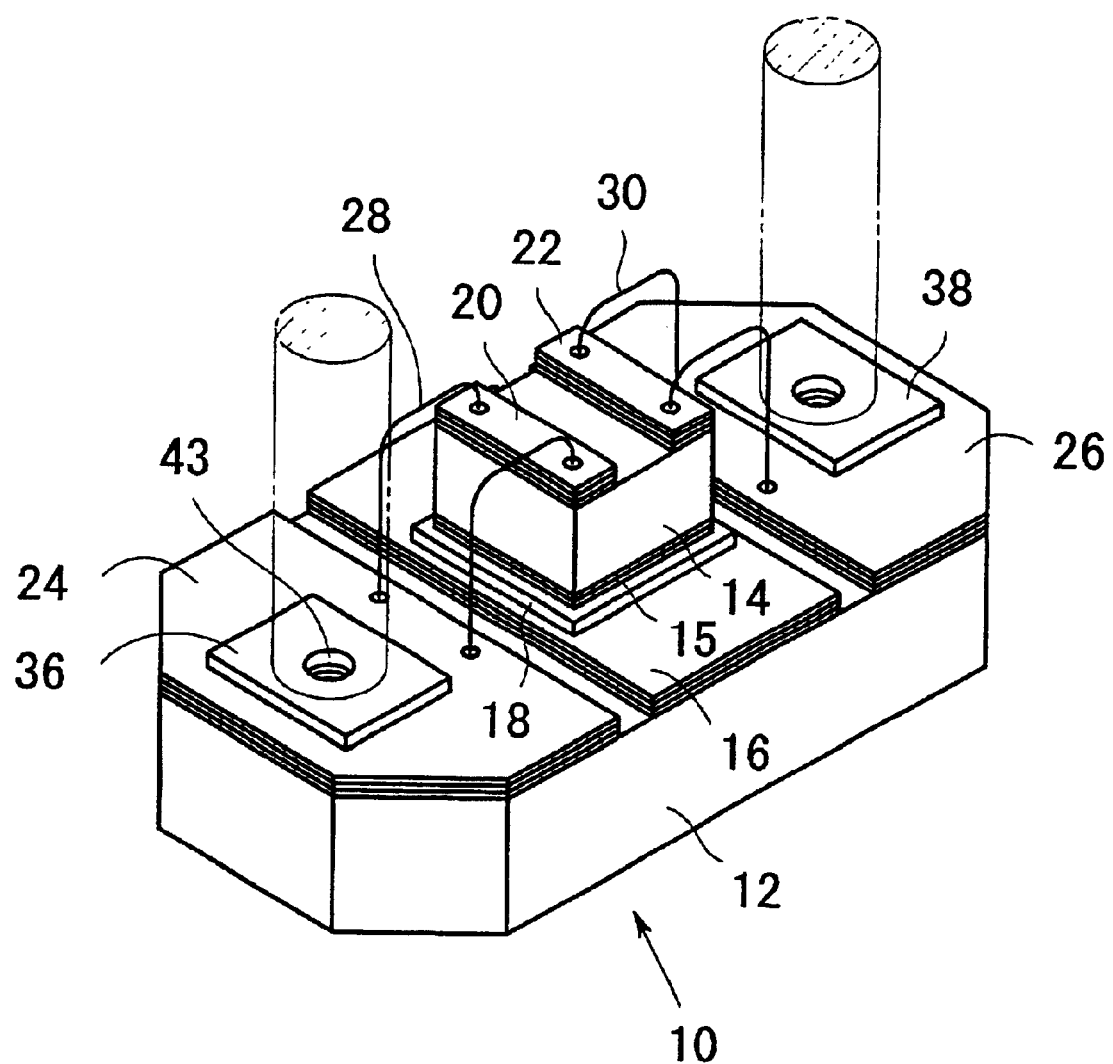
FIG. 1 is a perspective view showing one embodiment of a sample assembly according to the invention.

Referring to FIG. 1 showing one embodiment of a sample assembly according to the invention, the sample assembly 10 is for a TSC analyzer and has a substrate 12, made of aluminum nitride, to which a GaAs sample 14 is bonded. The aluminum nitride is a highly heat-conductive, electrically-insulating material. Since it is important for the TSC analyzer to control the sample temperature precisely and uniformly, the thermal conductivity of the substrate 12 must be good. The thermal conductivity of the aluminum nitride is 170 [W/(m·K)] at 20° C. which is very good. The material of the substrate 12 alternatively may be boron nitride, beryllium oxide or aluminum oxide: stating their thermal conductivity values in [W/(m·K)], boron nitride is 75 (noting that it has directional dependency) at 20° C., beryllium oxide is 240 at 20° C., and aluminum oxide is 38 at 20° C.

The long substrate 12 has a longitudinally-central region, on which an intermediate layer 16 is deposited by vacuum evaporation (preferably electron beam evaporation). The intermediate layer 16 is made of a multilayer having a three-layered structure of Ti/Mo/Au. That is, Ti (titanium), Mo (molybdenum) and Au (gold) are deposited in the described order from the substrate side, namely the top layer being a gold layer.

The substrate 12 has the two longitudinally-end regions, on which a pair of junction electrode layers 24 and 26 are deposited by vacuum evaporation with certain distances from the central intermediate layer 16. Each of these junction electrode layers 24 and 26 also is made of a multilayer having a three-layered structure of Ti/Mo/Au similarly to the central intermediate layer 16, the top layer being, of course, a gold layer. The bottom Ti layer gives an anchoring effect which makes the multilayer firmly bonded to the aluminum nitride substrate 12, resulting in an improved adhesion strength of the multilayer. The intermediate Mo layer performs a function of retarding Ti diffusion from the bottom Ti layer to the top Au layer. When Ti diffuses into Au, the work function of Au disadvantageously varies, causing a noise electromotive force. The top Au layer performs a function of ensuring an Ohmic contact with an Au wire which will be described below, resulting in easy wire bonding. The junction electrode layers 24 and 26 and the intermediate layer 16 are of the same structure, so that these layers can be made by the same thin-film deposition processes. Stating the thickness of the layers, Ti is about 50 nm, Mo is about 100 nm and Au is about 1 $\mu$m. The above-mentioned Mo may be replaced by Pt, that is, a three-layered structure of Ti/Pt/Au may be used for each of the junction electrode layers 24 and 26 and the intermediate layer 16.

On the intermediate layer 16 is bonded the GaAs sample 14 via an adhesive layer 18 which is made of In (indium). The adhesive layer 18 is 8 to 100 $\mu$m in thickness. The sample 14 is 5 mm×5 mm in plane size (a size in a plane parallel to the substrate surface) and 625 $\mu$m in thickness.

The indium, which constitutes the adhesive layer, has extremely high thermal conductivity, resulting in good temperature uniformity in the sample. Since the crystal defect analysis for GaAs using the TSC measurement requires sample temperature stability of less than 0.2° C., the sample must be controlled to an uniform temperature, which is accomplished by the use of the indium for the adhesive. The indium has thermal conductivity of 81.6 [W/(m·K)] at 27° C., while the silver paste, which is the conventional adhesive, has thermal conductivity of 4 [W/(m·K)] at 25° C., that is, the indium is about twenty times, in thermal conductivity, larger than the silver paste. The Indium may be replaced by AuSn (gold-tin) alloy which also has high thermal conductivity, for example, 80% Au-20% Sn alloy is 57.3 [W/(m·K)] at 20° C.

Besides, the indium, which constitutes the adhesive layer, has a melting point of about 157° C. and therefore can be melted easily by heating the sample assembly 10 to about 180° C. so that the sample 14, which has been analyzed, can be removed from the substrate 12. After the removal, another sample 14 may be bonded to the same substrate 12 with the use of the indium, resulting in the reuse of the substrate 12. In this case, the Au wires, which have been connected to the analyzed sample 14, are removed and new Au wires are used to make wire bonding with the new sample. The junction electrode layers 24 and 26 on the substrate are reusable several times: that is, the layer having a Ti/Mo/Au structure deposited by electron beam evaporation is reusable several times, while the layer having a Ti/Pt/Au structure deposited by sputtering is reusable more times because of its good physical strength against thermal hysteresis.

In the case of using "silver past including epoxy resin" as in the prior art, the substrate is not reusable. In the case of using AuSn alloy instead of the indium in the invention, it would be difficult to reuse the substrate because of its higher melting point of about 240° C. for 88% Au-12% Sn.

The intermediate layer 16 formed on the substrate 12 gives a function of increasing adhesive performance between the adhesive layer 18 and the substrate 12. If the indium adhesive layer 18 is in contact directly with the substrate 12, wettability becomes poor between the adhesive layer 18 and the substrate 12.

The sample 14 has the bottom surface covered with a two-layered film 15 which consists of Ti (titanium) and Au (gold) layers in the described order from the sample side. Accordingly, at the region at which the sample 14 is bonded to the substrate 12, layers of Ti/Mo/Au/In/Au/Ti are to be arranged, in the described order from the substrate side, between the aluminum nitride substrate 12 and the GaAs sample 14.

Next, thermal stress between the sample and the substrate will be explained. The sample and the substrate are made of different materials and thus have different rates of linear expansion. Therefore, if the sample temperature varies under the bonded condition to the substrate, the extent of thermal expansion differs between the sample and the substrate because of their different rates of linear expansion, generating thermal stress at the bonding surface between the sample and the substrate. As the bonding area between the sample and the substrate becomes larger, the thermal stress becomes higher. Especially, higher thermal stress occurs at the periphery of the bonding area than at the center. High thermal stress gives rise to a problem such as cracking in the sample or in the substrate. Besides, the thermal stress may have an influence on the measured data which is an extremely feeble current. Therefore, it is important not to make a wide adhesive area (i.e., the sample plane size) between the sample and the substrate so that the thermal stress becomes not so high. In the embodiment shown in FIG. 1, the plane size of the sample 14 is 5 mm×5 mm as described above. With such an extent of the size, the influence of the thermal stress would not be so high, resulting in actually no problem such as cracking in the sample or in the substrate. In view of the thermal stress, the sample size may preferably be less than the above-mentioned size. The small sample size gives the further advantage of increased temperature uniformity in the sample, that is, the temperature distribution becomes small in the sample.

In should be noted that the extent of the thermal stress depends upon not only the sample size but also, of course, the respective rates of linear expansion of the sample, the substrate and the adhesive layer therebetween. It is further considered that the thermal stress depends upon also the respective thickness of the sample and the adhesive layer. Stating such parameters in this embodiment, the rate of linear expansion of GaAs, which is the material of the sample 14, is $5.8 \times 10^{-6}$ [1/K], and the rate of linear expansion of indium, which is the material of the adhesive layer 18, is $3.3 \times 10^{-5}$ [1/K], and the rate of linear expansion of aluminum nitride, which is the material of the substrate 12, is $3.9 \times 10^{-6}$ [1/K]. The thickness of the sample 14 is 625 μm and the thickness of the adhesive layer 18 is, for example, 8 μm. Strictly speaking, it should be understood that, only under the specific condition of a combination of such materials and the thickness, the plane size of the sample is preferably 5 mm×5 mm or less as described above. However, even when the materials and the thickness differ from the above-described condition, the limitation of the sample plane size, 5 mm×5 mm or less in view of the thermal stress, would be effective as long as the rates of linear expansion and the thickness do not greatly differ from the above-described values.

Next, electrode layers formed on the top surface of the sample 14 will be explained. The sample 14 has the top surface on which a pair of electrode layers 20 and 22 are deposited by vacuum evaporation with a distance therebetween. Each of the electrode layers 20 and 22 is made of a multilayer which has a three-layered structure of AuGe/Ni/Au, that is, layers of 88% Au-12% Ge (gold-germanium) alloy, Ni (nickel) and Au (gold) are deposited in the described order from the sample side, namely the top layer being a gold layer. Such a three-layered structure is for Ormic contact between the Au wires and the sample electrodes. The bottom layer made of AuGe alloy gives a function of increasing adhesion strength between the GaAs sample 14 and the electrode layer. Stating the thickness of the layers, AuGe is about 50 nm, Ni is about 10 nm and Au is about 500 nm.

The sample 14 has, on its surface, the left electrode layer 20 having the top layer (Au) which is electrically connected to the top layer (Au) of the left junction electrode layer 24 via two Au wires 28. Similarly, the sample 14 has, on its surface, the right electrode layer 22 having the top layer (Au) which is electrically connected to the top layer (Au) of the right junction electrode layer 26 via other two Au wires 30. The Au wires may be replaced by Pt wires or Al (aluminum) wires, noting that, in that case, it is important to make the respective top layers of the electrode layers 20 and 22 and the junction electrode layers 24 and 26 the same material as the wires.

Figure 2:
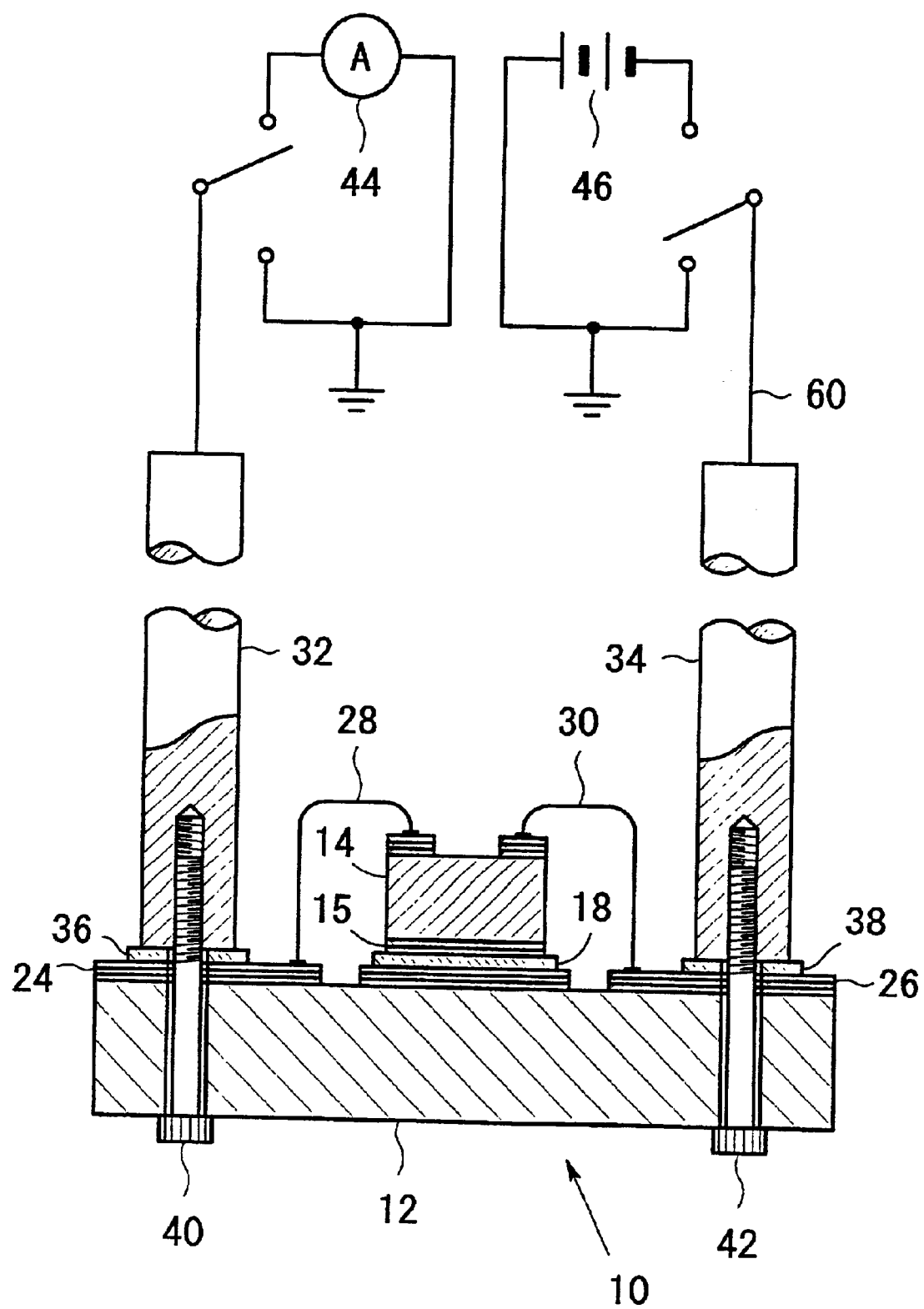
FIG. 2 is a cross-sectional elevation showing the sample assembly and its support structure and electric circuit.

Next, the support structure, with which the sample assembly 10 is supported in a TSC analyzer, will be explained. FIG. 2 is a cross-sectional elevation showing the sample assembly and its support structure and electric circuit. The sample assembly 10 is supported, in a TSC analyzer, by two support rods 32 and 34 made of stainless steel. These support rods 32 and 34 serve also as conductors for making an electric circuit.

The left support rod 32 is joined to the substrate 12 of the sample assembly 10 by a screw 40. A gold washer 36 is inserted between the bottom surface of the support rod 32 and the top surface of the left junction electrode 24. Each of the substrate 12, the junction electrode layer 24 and the Au washer 36 has a penetration 43 (see FIG. 1) through which the screw 40 can penetrate. The support rod 32 has a lower portion having an internal thread with which the screw 40 can engage. The right support rod 34 is similarly joined to the substrate 12 by another screw 42 and another Au washer 38. If the Au washers 36 and 38 are not inserted, the substrate 12 made of aluminum nitride might be broken or the junction electrode layers 24 and 26 may have cracks because of the thermal displacement (expansion or contraction caused by temperature variation) of the support rods 32 and 34 made of stainless steel under wide-range temperature variation, for example, between the liquid nitrogen temperature and the room temperature. Inserting the Au washers 36 and 38 solves such a problem.

Between the pair of support rods 32 and 34 are selectively connected an ammeter 44 and a voltage source 46. Lead cables 60, which are connected with the support rods 32 and 34, are triple-shielded cables, expecting noise reduction.

Figure 3:
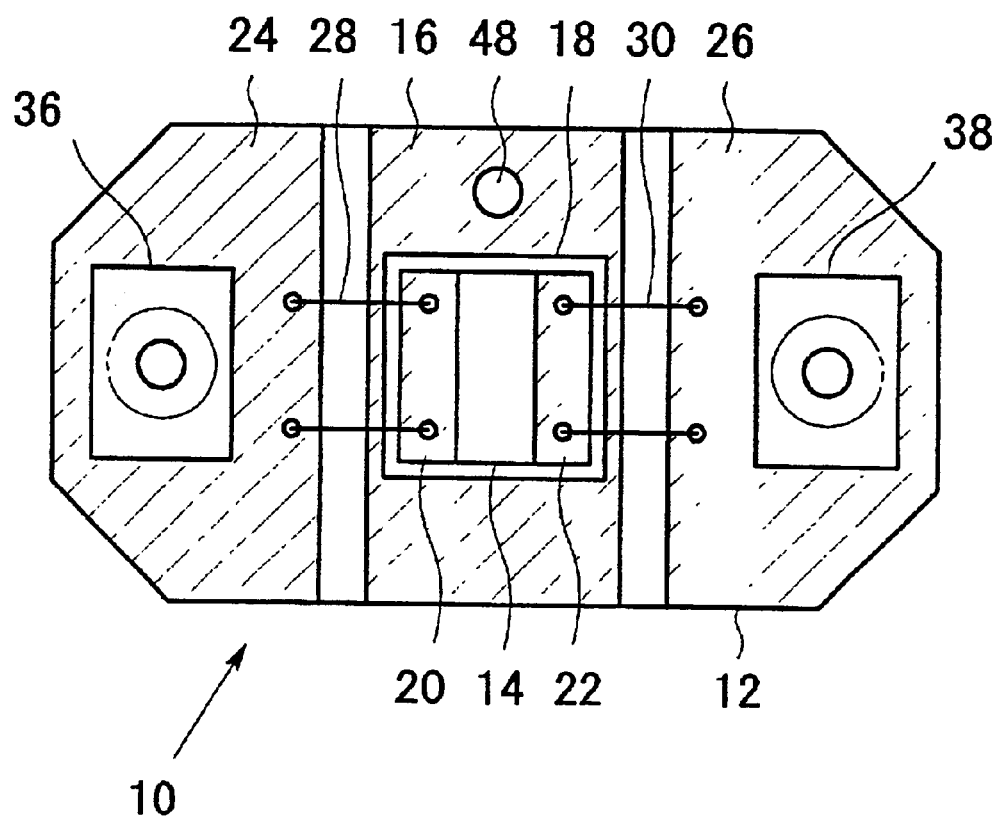
FIG. 3 is a plan view of the sample assembly.

FIG. 3 is a plan view of the sample assembly 10. The intermediate layer 16 and the junction electrode layers 24 and 26 formed on the substrate 12 are illustrated by hatching, and the electrode layers 20 and 22 formed on the sample 14 are also illustrated by hatching. The substrate 12 has, near its center, a hole 48 into which a platinum resistance thermometer (or a thermocouple) is to be inserted.

Since the sample assembly 10 includes the sample 14 having the top surface on which the pair of electrode layers 20 and 22 are formed, a thermally stimulated current along the surface of the sample 14 can be measured. That is, the sample assembly 10 enables crystal defect analysis in the vicinity of the surface of the sample.

As can be seen from FIG. 3, the pair of the electrode layers 20 and 22 on the sample, the pair of the junction electrode layers 24 and 26 on the substrate and the wires 28 and 30, in this sample assembly 10, are mirror-symmetrical with respect to the center of the sample 14, so that even when the contact-electromotive force and/or the thermoelectromotive force occur, such electromotive forces can be cancelled.

Figure 4:
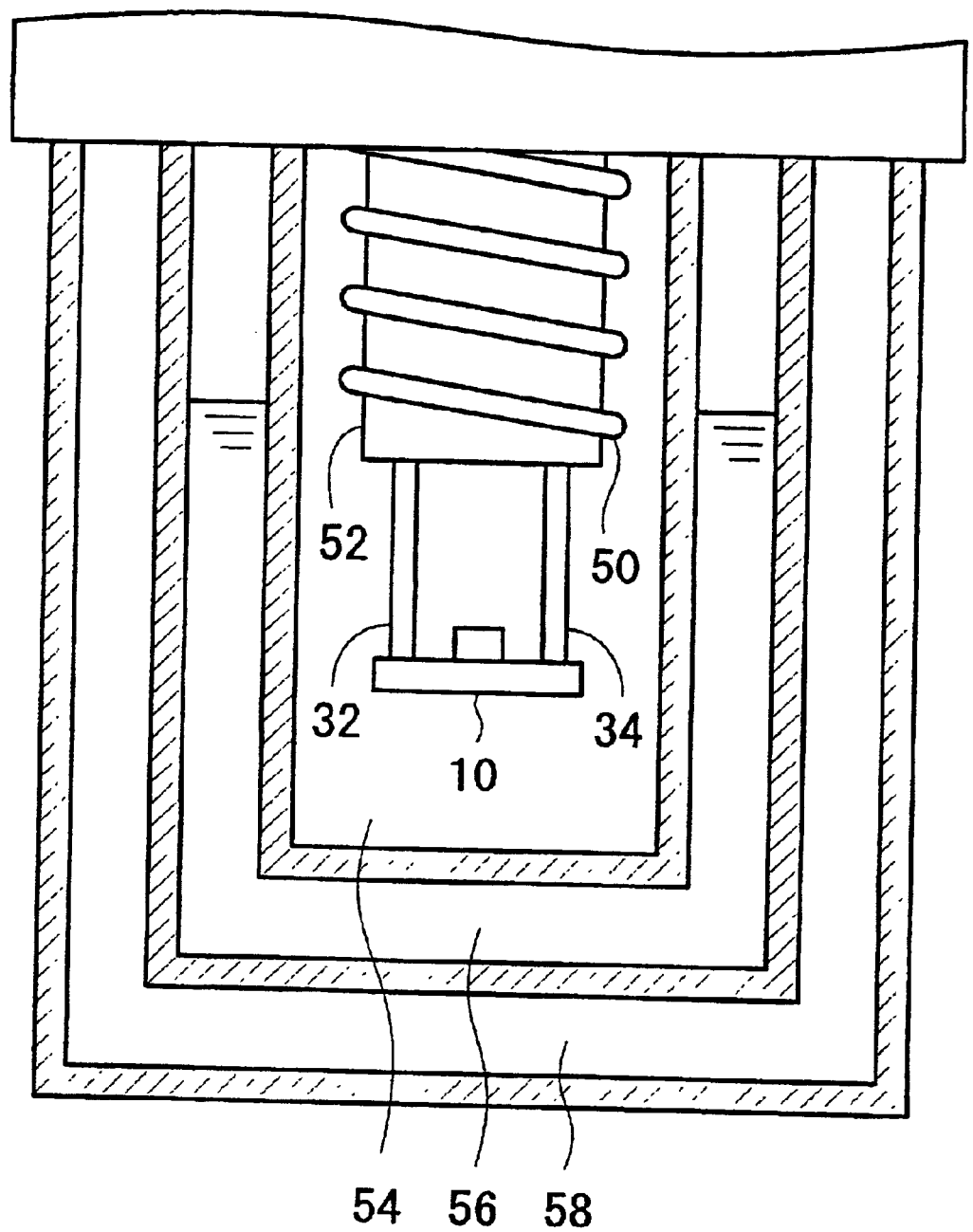
FIG. 4 is a cross-sectional elevation showing schematically a surrounding structure of the sample assembly in a TSC analyzer.

FIG. 4 is a cross-sectional elevation showing schematically a surrounding structure of the sample assembly in a TSC analyzer. The sample assembly 10 is supported by the pair of support rods 32 and 34. A cylindrical cover 52, on which a heater coil 50 is wound, is movable vertically. The cover 52 is moved down to cover the surroundings of the sample assembly 10. The space 54, which houses the sample assembly 10, is filled with helium gas. The outer space 56 is filled with liquid nitrogen. The further outer space 58 is evacuated to vacuum.

Figure 5:
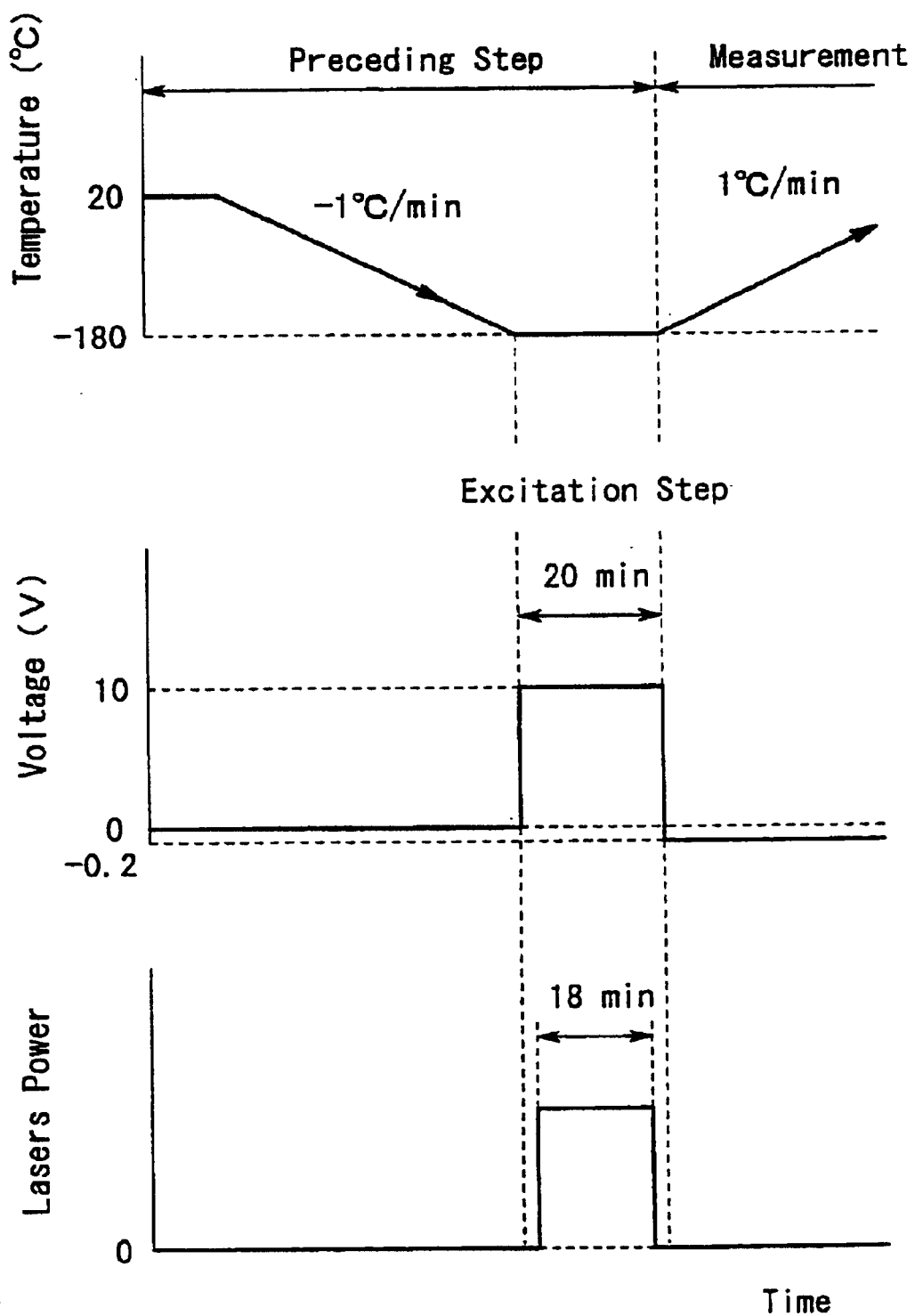
FIG. 5 is a graph showing an example of a TSC measurement program using the sample assembly shown in FIG. 1.

FIG. 5 is a graph showing an example of a TSC measurement program using the sample assembly shown in FIG. 1. First, the sample temperature is decreased from the room temperature (for example 20° C.) to minus 180° C. with the temperature gradient of 1° C. a minute. Next, a voltage of 10 V is applied to the sample for twenty minutes with the sample temperature remaining at minus 180° C. Within the voltage application period, the sample is exposed to lasers for eighteen minutes. The voltage application and the lasers exposure make the crystal defect in the GaAs sample an excited state. Thereafter, the sample temperature is increased from minus 180° C. to the room temperature with the temperature gradient of 1° C. a minute under the condition that a voltage of minus 0.2 V is applied to the sample. As the temperature is increased, the above-described excited state is relaxed, generating a feeble current (for example, an order of $10^{-13}$ to $10^{-15}$ ampere) in the sample. The current is measured versus temperature to obtain a TSC spectrum which is analyzed to know the state of the crystal defects in the sample.

What is claimed is:

1. A sample assembly for a thermoelectric analyzer comprising:
   (a) an electrically-insulating substrate having a longitudinally-central region and two longitudinally-end regions;
   (b) an adhesive layer disposed on said longitudinally-central region and made of a material selected from a group consisting of indium and gold-tin alloy;
   (c) a pair of junction electrode layers formed on said two longitudinally-end regions respectively with certain distances from said adhesive layer;
   (d) a sample fixed to said adhesive layer, said sample being for thermostatic analysis in which an electric property of said sample is measured as a temperature of said sample varies;
   (e) a pair of electrode layers formed on a top surface of said sample;
   (f) a first electrically-conductive wire connecting one of said electrode layers with one of said junction electrode layers; and
   (g) a second electrically-conductive wire connecting the other of said electrode layers with the other of said junction electrode layers wherein an electrical property of the sample is measured as a temperature of the sample varies.

2. A sample assembly according to claim 1, wherein said adhesive layer is made of indium.

3. A sample assembly according to claim 2, wherein said substrate is made of a material selected from a group consisting of aluminum nitride, boron nitride, beryllium oxide and aluminum oxide.

4. A sample assembly according to claim 3, wherein each of said electrode layers and said junction electrode layers is a multilayer including a top layer which is a gold layer, and said first and second electrically-conductive wires are gold wires.

5. A sample assembly according to claim 4, wherein said pair or electrode layers, said pair of junction electrode layers and said first and second electrically-conductive wires are arranged mirror-symmetrical with respect to a center of said sample.

6. A sample assembly according to claim 5, wherein said sample is a compound semiconductor.

7. A sample assembly according to claim 1, wherein said adhesive layer is made of a gold-tin alloy.

8. A sample assembly according to claim 1, wherein said substrate is made of a material selected from a group consisting of aluminum nitride, boron nitride, beryllium oxide and aluminum oxide.

9. A sample assembly according to claim 1, wherein said sample assembly is adapted to be supported by two support rods which also serve as conductors for an electric circuit, and wherein gold washers are inserted between said support rods and said junction electrode layers.

10. A sample assembly according to claim 1, wherein each of said electrode layers and said junction electrode layers is a multilayer including a top layer which is a gold layer, and said first and second electrically-conductive wires are cold wires.

11. A sample assembly according to claim 1, wherein said pair of electrode layers, said pair of junction electrode layers and said first and second electrically-conductive wires are arranged mirror-symmetrical with respect to a center of said sample.

12. A sample assembly according to claim 1, wherein said sample is a compound semiconductor.

13. A sample assembly according to claim 1, wherein said sample has a plane size of 5 mm×5 mm or less.

* * * * *